(12) United States Patent  
Tokunaga et al.

(10) Patent No.: US 7,040,170 B2  
(45) Date of Patent: May 9, 2006

(54) METHODS FOR MEASURING STRENGTH OF FILM AND DETERMINING QUALITY OF OBJECT HAVING THE FILM

(75) Inventors: Yuichiro Tokunaga, Kyoto-fu (JP); Takeshi Inao, Kyoto-fu (JP)

(73) Assignee: Murata Manufacturing Co., Ltd., (JP)

( * ) Notice: Subject to any disclaimer, the term of this patent is extended or adjusted under 35 U.S.C. 154(b) by 0 days.

(21) Appl. No.: 10/891,341

(22) Filed: Jul. 13, 2004

(65) Prior Publication Data

US 2005/0039534 A1 Feb. 24, 2005

(30) Foreign Application Priority Data

Aug. 21, 2003 (JP) .............................. 2003-297862

(51) Int. Cl.  
*G01N 29/00* (2006.01)  
*G01B 17/00* (2006.01)

(52) U.S. Cl. .............................. 73/620; 73/629; 73/646

(58) Field of Classification Search .......... 73/596–600, 73/602, 620–625, 627–629, 645–646  
See application file for complete search history.

(56) References Cited

U.S. PATENT DOCUMENTS

| 5,271,274 | A | * | 12/1993 | Khuri-Yakub et al. | ........ 73/597 |
| 5,513,531 | A | * | 5/1996 | Sapia et al. | .................... 73/602 |
| 6,799,472 | B1 | * | 10/2004 | Nakayama et al. | ............ 73/827 |

FOREIGN PATENT DOCUMENTS

| JP | 63-82312 | * | 4/1988 |
| JP | 1-113606 | * | 5/1989 |
| JP | 02-051060 | | 2/1990 |
| JP | 2-296104 | * | 12/1990 |

* cited by examiner

*Primary Examiner*—Helen Kwok  
(74) *Attorney, Agent, or Firm*—Ostrolenk, Faber, Gerb & Soffen, LLP (57) ABSTRACT

A method for measuring a film strength of a film on an object. An incident angle of pressure waves with respect to an object to be measured, the object including a base coated with a film, is set for applying the pressure waves to the object. The incident angle is varied over a range including a critical angle $\theta cr$. The object generates surface waves, in response to the pressure waves, at and near the critical angle. In response to the surface waves, the object generates leaky waves, which are pressure waves caused by the surface waves. The intensity of pressure waves including reflected waves and leaky waves from the object are measured. A received intensity $V_0$ at an incident angle where no leaky wave is generated, and the intensity difference $V_C$ between $V_0$ and the received intensity at the critical angle $\theta cr$ when the film strength is high are measured. An intensity difference $V_R$ between $V_0$ and the received intensity when the intensity of the leaky waves remains unchanged, regardless of the changes in the incident angle, within the range where the leaky waves are generated, which indicates a low film strength, is also measured. Thus, the film strength is determined based on $V_0$, $V_C$, and $V_R$.

11 Claims, 8 Drawing Sheets

FREQUENCY (Hz)

METHODS FOR MEASURING STRENGTH OF FILM AND DETERMINING QUALITY OF OBJECT HAVING THE FILM

BACKGROUND OF THE INVENTION

1. Field of the Invention

The present invention relates to simple methods for measuring the strength of a film and determining the quality of an object to be measured, the object having the film.

2. Description of the Related Art

For an electronic component having a film, such as an external electrode, on the surface, it is important for exhibiting stable performance to increase the strength of the film and prevent the separation of the film. If an electronic component is the object to be measured, there are a variety of known methods for determining the property constants of the film, structural parameters such as the film thickness, and the presence of cracks and separations. For example, Japanese Examined Patent Application Publication No. 7-9418 (published on Feb. 1, 1995) discloses a method using a spectrum ultrasonic microscope that can perform two-dimensional and quantitative measurement and detection on a surface of an object to be measured.

In the spectrum ultrasonic microscope, an impulse generator transmits pulse signals to a transmitting transducer, which then changes the frequency of the ultrasonic waves corresponding to the pulse signals and applies the ultrasonic waves to the object to be measured. Reflected waves from the object are received by a receiving transducer, transformed into electric signals, and output. Received and amplified electric signals are analyzed by a spectrum analyzer serving as a frequency analyzer and converted from analog to digital. In a computer, an obtained frequency distribution undergoes a feature subtraction process in a digital-operation unit, as programmed by an operator. A resulting frequency distribution is stored in a storage unit and displayed in an image output unit. An X-Y-stage-driving unit connected to a stage for mounting the object to be measured is X-Y scanned in synchronization with signals from the impulse generator.

According to this structure, acoustic waves are applied to the object at a constant incident angle. The data obtained by receiving the reflected waves enable the property constants of the object, structural parameters such as the film thickness, and the presence of cracks and separations to be two-dimensionally and quantitatively measured and detected on the surface of the object.

Figure 8:
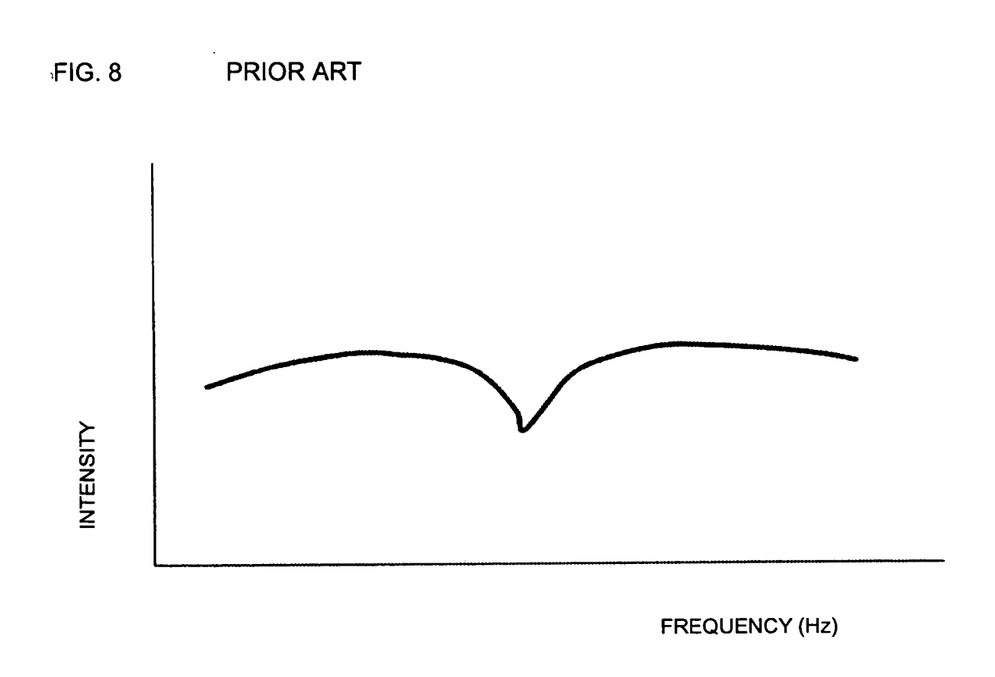
FIG. 8 is a graph showing a measurement result used in a known method for determining the presence of a separation.

In the method described in Japanese Examined Patent Application Publication No. 7-9418, pressure waves having wideband frequency components are applied to the object at a constant angle. Pressure waves reflected from the object are then processed by a fast Fourier transform (FFT) method. As shown in FIG. 8, a frequency corresponding to a minimum intensity is detected. Thus, the film thickness and the presence or absence of the film separation can be detected, and state changes on the surface of the object can be determined.

In the method described above, a film and a base firmly bonded together can be distinguished from a film and a base sandwiching a middle layer made of a different material, or from a film and a base totally separated from each other. However, since a film weakly bonded to a base material (defective) and a film firmly bonded to a base (normal) are similarly indicated, they cannot be distinguished from one another and the bond strength of a film cannot be quantitatively determined in this method.

SUMMARY OF THE INVENTION

To solve the problem described above, the method for measuring a film strength according to the present invention includes the steps of setting an incident angle of pressure waves with respect to an object to be measured, the object including a base coated with a film, for applying the pressure waves to the object; varying the incident angle over a range including a critical angle, allowing the object to generate surface waves, in response to the pressure waves, at and near the critical angle; and thereby allowing the object to generate leaky waves, the leaky waves being pressure waves caused by the surface waves; measuring the intensity of the pressure waves from the object, the pressure waves including reflected waves and the leaky waves; and determining the film strength of the object based on changes in the intensity of the leaky waves from the object in response to changes in the incident angle.

In this method, the intensity of the pressure waves from the object is measured while the incident angle of the pressure waves (ultrasonic waves) applied to the object is varied over a range including the critical angle. The relationship between the pressure waves to the object and the intensity of the pressure waves from the object is thus determined.

When the film strength of the object is low due to, for example, a film separation, the film is deformed by the surface waves accordingly. Then, the propagation of the leaky waves caused by the surface waves is inhibited, and the intensity of the leaky waves from the object remains unchanged in some regions depending on the film strength.

Thus, in this method, film strength can be quantitatively measured and the peel strength of a film is quantitatively assessed based on the amount and location of changes in the intensity of leaky waves, which correspond to the film strength.

In the method for measuring a film strength described above, the step of determining the film strength of the object may further include the substep of determining whether a film separation occurs in the object, based on the presence or absence of a region where the intensity of the leaky waves remains unchanged regardless of the changes in the incident angle.

The method for measuring a film strength described above may further include the steps of measuring the film strength of each of a plurality of objects, and comparing the measured film strengths to evaluate the film strength of each of the objects relatively.

A method for measuring a film strength, according to another aspect of the present invention, includes the steps of setting an incident angle of pressure waves with respect to an object to be measured, the object having a film on a surface; applying the pressure waves to the object; and measuring pressure waves including reflected waves and leaky waves from the object to determine the strength of the film. The method is characterized by the steps of preparing, in advance, a first reference sample having no separation and made of a material similar to that of the object, applying the pressure waves to the first reference sample at varying incident angles, measuring the intensity of the pressure waves from the object, the intensity including a first intensity when the incident angle of the pressure waves is a critical angle and the leaky-wave intensity is high, and a second intensity when no leaky-wave intensity is detected, and thereby determining an intensity difference $V_C$ between the first intensity and the second intensity; preparing, in advance, a plurality of second reference samples each having separations and being made of a material similar to that of the object, applying the pressure waves to the second reference samples at varying incident angles over the range including the critical angle, measuring the intensity of the pressure waves from the object; and thereby determining an intensity difference $V_R$ between a third intensity when the leaky-wave intensity remains unchanged over a range of incident angle, and the second intensity; measuring a peel strength of each second reference sample by an actual measurement to determine a relationship between the obtained peel strength and a bond strength index a; applying the pressure waves to the second reference samples at varying incident angles over the range including the critical angle, measuring the intensity of the pressure waves from the object, and thereby determining the intensity difference $V_R$ of the object; and determining the peel strength of the film of the object based on the relationship between the peel strength and the bond strength index a, and the intensity difference $V_R$ of the object.

In the method for measuring a film strength described above, the step of determining the peel strength of the film of the object may utilize the equation $a=(V_R V_0) V_C^2$, where $V_0$ is the second intensity.

The method for measuring a film strength described above preferably includes the step of immersing the object in an inelastic fluid in advance. Thus, pressure waves are promptly and reliably transmitted in the inelastic fluid and reliable measurement can be achieved. Moreover, when a film is deformed by surface waves, a gap generated between a surface of the object and the inelastic fluid reliably inhibits the transmission of leaky waves, and thus improves the measurement accuracy of the film strength.

A method for determining the quality of an object having a film according to the present invention is characterized by determining the quality of the object based on the presence or absence of a film separation, through the use of the method for measuring a film strength described above.

With this method for measuring a film strength according to the present invention, reliable and simple detection of a film separation can be achieved. Thus, stable determination of the quality of the object can be made.

In the method for determining the quality of an object having a film, a criterion for determining the quality of the object can be changed by changing the output of the pressure waves to be applied to the object.

According to this method, surface waves excited by pressure waves are changed by changing the output of the pressure waves, and thus the criterion for determining the quality of the object can be changed. For example, an increase in the output of the pressure waves increases the intensity of the surface waves, which then increases a peel stress in a film. Thus, a stricter criterion can be set up for determining the quality of the object.

The method for measuring a film strength according to the present invention includes the steps of varying an incident angle of pressure waves (ultrasonic waves), with respect to an object having a film, over a range including a critical angle, applying the pressure waves to the object at and near the critical angle, allowing the object to generate leaky waves caused by surface waves, and thereby measuring changes in intensity of the leaky waves from the object so as to measure the intensity of the film.

In this method, the peel strength of a film can be quantitatively assessed by measuring changes in the intensity of leaky waves from an object. Therefore, the film strength of an object without deformation but having low film strength, as well as the film strength of an object with deformation including floating, separations, and scratches, can be measured. Thus, the method is suitable for use in producing an electronic component having a film, such as an external electrode.

Other features and advantages of the present invention will become apparent from the following description of embodiments of the invention which refers to the accompanying drawings.

DESCRIPTION OF EMBODIMENTS OF THE INVENTION

Embodiments of the present invention will now be described with reference to FIGS. 1 to 7.

First Embodiment

Figure 2:
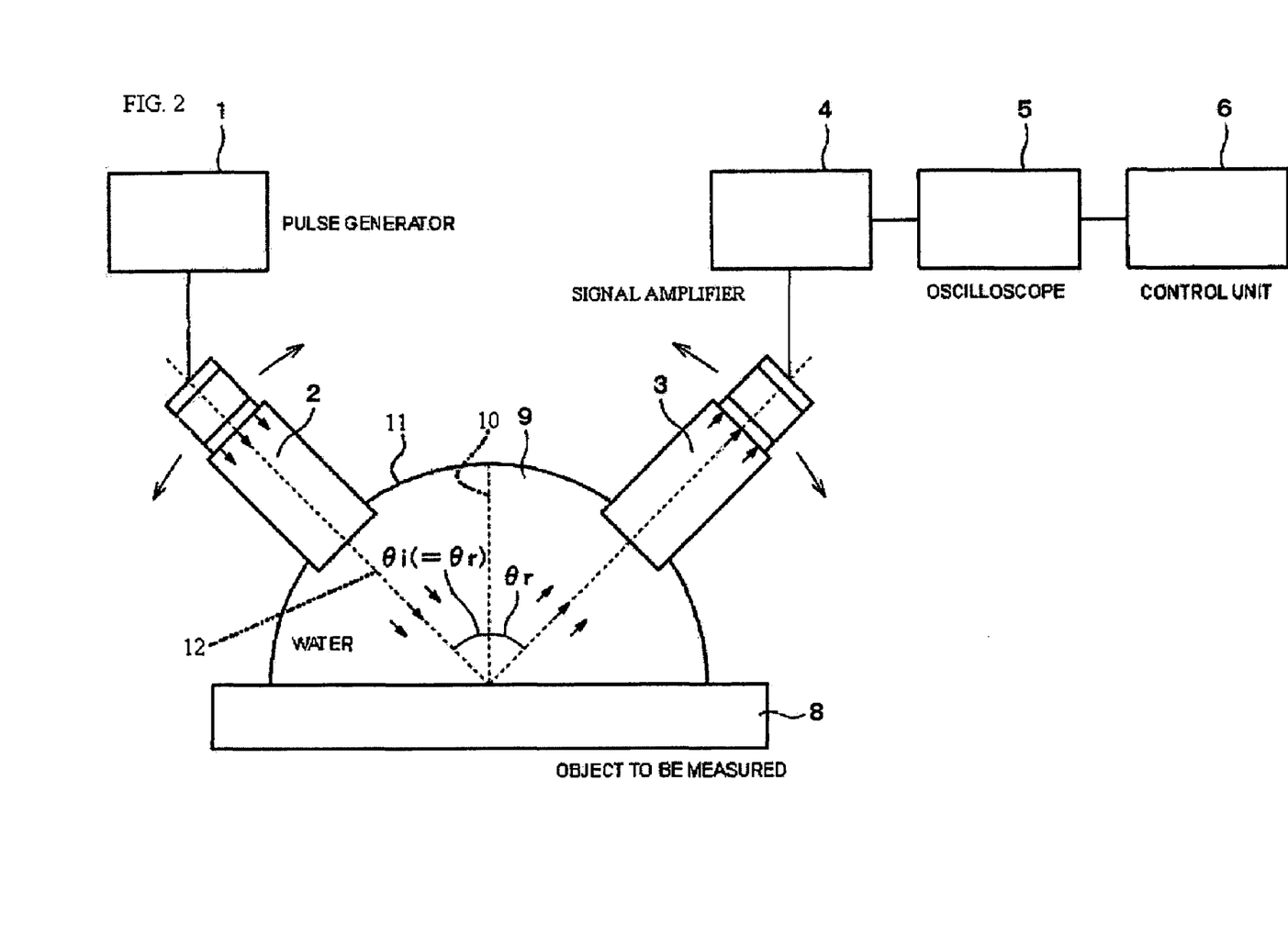
FIG. 2 is a block diagram of a measuring apparatus used in the method for measuring film strength.

As shown in FIG. 2, a measuring apparatus used in the method for measuring film strength according to a first embodiment of the present invention has a box-shaped main body (not shown) with a bottom to which an object 8 to be measured can be secured. Water 9 can be poured into the main body of the measuring apparatus such that the object 8 is completely submerged (immersed).

In the object 8, a film is deposited on a base, such as a substrate. For example, a gold (Au)-evaporated film is deposited to a thickness of 100 nm on a lithium niobate wafer serving as a base material. As another example, the object 8 may be one in which an Au-sputtered film is deposited to a thickness of 10 nm on a silicon wafer serving as a base material.

The water 9 may be replaced with any type of inelastic fluid that can efficiently transmit pressure waves (ultrasonic waves, longitudinal waves). For example, the water 9 may be replaced with alcohol, such as ethanol.

A columnar transducer 2, such as a piezoelectric element, which transforms electric signals into mechanical vibrations for supplying pressure waves, is mounted to the main body of the measuring apparatus such that the pressure waves are applied to the surface of the object 8. The transducer 2 is arranged such that an outlet for supplying the pressure waves is immersed in the water 9.

The transducer 2 is mounted such that an incident angle θi of the pressure waves with respect to the object 8 can be adjusted. Therefore, a driving unit (not shown) is provided so as to move the transducer 2, in the main body of the measuring apparatus, along a semicircle 11, the semicircular path being shown schematically in FIG. 2. A radial line 10 bisecting the semicircle is defined orthogonal to the bottom surface of the main body (not shown). The incident angle θi is the angle between the center line 12 of the pressure waves applied to the object 8 and the normal line to the surface of the object 8, which coincides with the center line 10 of the semicircle 11.

In addition, a columnar transducer 3, such as a piezoelectric element, which receives and transforms pressure waves and outputs electric signals, is mounted to the main body of the measuring apparatus such that a receiving angle θr between the center line of the received pressure waves and the normal line described above can be adjusted. The transducer 3 is arranged such that an inlet of the transducer 3 is immersed in the water 9, similarly to the outlet of the transducer 2.

Another driving unit (not shown) is provided so as to move the transducer 3, in the main body of the measuring apparatus, along the semicircle 11.

The transducers 2 and 3 are preferably driven along the semicircle 11 in an integrated manner such that the incident angle θi and the receiving angle θr remain substantially the same.

Moreover, another driving unit may be provided to rotate the transducers 2 and 3 substantially about the above-described normal line 10 and substantially parallel to the bottom surface of the main body (not shown) of the measuring apparatus. The transducers 2 and 3 are preferably rotated in an integrated manner.

A measuring apparatus of the first embodiment includes a pulse generator 1, a signal amplifier 4, an oscilloscope 5, and a control unit 6. The pulse generator 1 generates and outputs pulses of varying voltages, that is, pulsed electric signals to the transducer 2. The signal amplifier 4 receives and electrically amplifies electric signals from the transducer 3, and outputs the electric signals to the oscilloscope 5. The oscilloscope 5 converts the electric signals from the signal amplifier 4 to be displayed.

The control unit 6 adjusts the angles of the transducers 2 and 3, while controlling the output of the pressure waves from the transducer 2 and the receiving sensitivity of the transducer 3 to the pressure waves. In addition, the control unit 6 has a function for analog-to-digital (A/D) conversion of the input electric signals, a memory storage for storing digitized electric signals, and a function for performing computations on the digitized electric signals.

The method for measuring film strength using the measuring apparatus will now be described. First, pulsed electric signals from the pulse generator 1 are applied to the transducer 2, which then generates pressure waves (ultrasonic waves, longitudinal waves). The incident angle θi of the pressure waves with respect to the object 8 having a film on the surface is set, and the pressure waves are applied through the water 9 to the object 8. Then, the transducer 3 receives, at the receiving angle θr, and detects pressure waves including reflected waves and leaky waves from the surface of the object 8. Electric signals corresponding to the received pressure waves, representing received intensity, are amplified by the signal amplifier 4, input into and displayed by the oscilloscope 5, and stored in the memory storage of the control unit 6.

While maintaining θi=θr, the above-described measuring apparatus varies θi and measures the received intensity at each of the varied incident angles θi. Here, the range of θi includes a critical angle θcr of the object 8. In other words, the received intensity is measured at θi over a range substantially centered on the critical angle θcr of the object 8.

The critical angle θcr is the incident angle that allows, when pressure waves are applied to the surface of the object 8, reflected waves to be generated at a reflection angle equal to the incident angle at which the pressure waves are applied. The critical angle θcr satisfies Snell's laws of refraction (Vs=Vw/sin θcr, where Vs is Rayleigh wave speed and Vw is sonic speed in water). An application of pressure waves, at a critical angle θcr, to the object 8 generates Rayleigh waves (surface waves) on the surface. The Rayleigh waves then causes the object 8 to generate leaky waves into the water 9.

The leaky waves, which are pressure waves phase-shifted (delayed) by π from reflected waves in the same direction, cancel out the reflected waves. Therefore, the measured intensity of the reflected waves, while the Rayleigh waves are generated, is reduced due to the intensity of the leaky waves corresponding to the intensity of the Rayleigh waves. Since the intensity of the leaky waves reaches a maximum value at the critical angle θcr, the received intensity of the pressure waves, including reflected waves and leaky waves, from the object 8 is reduced to a minimum value at the critical angle θcr.

Figure 3:
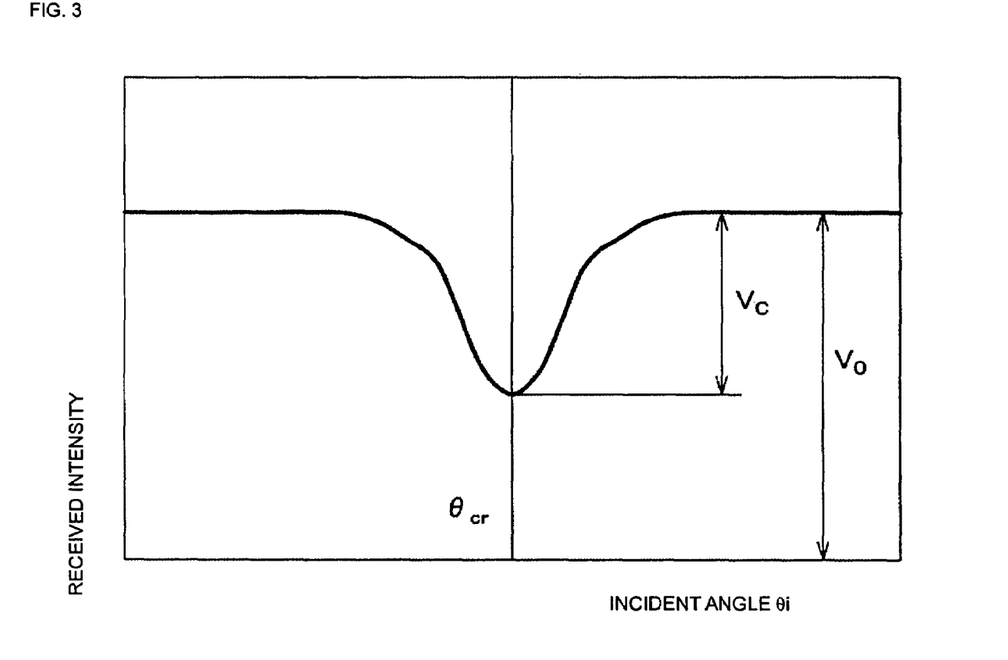
FIG. 3 is a graph showing changes in leaky waves from an object having a film when the film strength is high, the object to be measured by the method for measuring film strength.

In this method for measuring film strength, a relationship between the incident angle θi and the received intensity, when a film is firmly bonded to a base (substrate), is as shown in FIG. 3. In the range of the incident angle θi where leaky waves are generated, the graph showing the change in the intensity of leaky waves is similar to a Gaussian distribution. In FIG. 3, $V_0$ indicates a received intensity of reflected waves at an incident angle where no leaky wave is generated. $V_C$ indicates the difference between $V_0$ and the received intensity at the critical angle θcr where the intensity of the leaky waves is at a maximum value.

As described above, the graph showing the change in the intensity of the leaky waves is similar to a Gaussian distribution in the range of the incident angle θi where the leaky waves are generated. One reason is that pressure waves (ultrasonic waves) from the transducer 2 have a frequency distribution and spread out before reaching the object 8. Another reason is surface roughness of the object 8.

Figure 1:
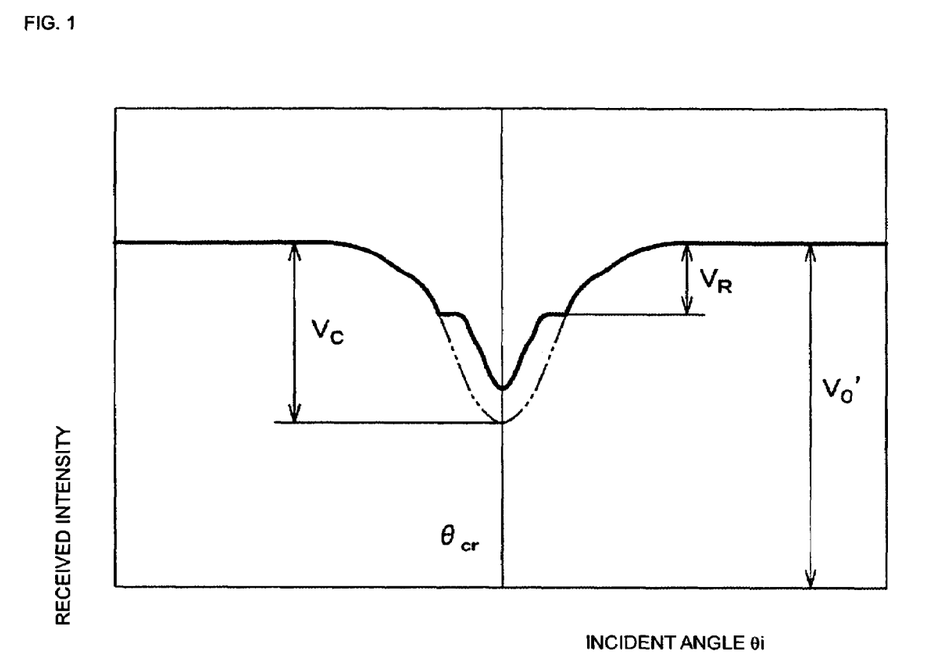
FIG. 1 is a graph showing changes in leaky waves from an object having a film when the film strength is low, the object being measured by a method for measuring film strength according to a first embodiment of the present invention.

On the other hand, FIG. 1 shows a relationship between the incident angle θi and the received intensity when the bond strength (peel strength) of a film is low (weak). As shown, there are some regions (steps) where the received intensity remains unchanged, even if the incident angle θi (together with the receiving angle θr) changes. $V_0'$ indicates a received intensity of reflected waves at an incident angle where no leaky wave is generated. $V_R$ indicates the difference between $V_0'$ and the received intensity in these regions. The received intensity is obtained by subtracting the intensity of the reflected waves from the intensity of the leaky waves, the reflected waves and the leaky waves being generated at the object 8. When the bond strength of a film is low, the propagation of the leaky waves to the water 9 is inhibited accordingly. Therefore, the apparent intensity of the leaky waves becomes constant in these regions.

When the bond strength of a film is low, Rayleigh waves cause a momentary deformation of the film accordingly. Thus, a gap, that is, a discontinuity layer is formed between the deformed portion of the film and the water 9, and blocks the propagation of the leaky waves from the object 8 to the water 9.

Figure 4:
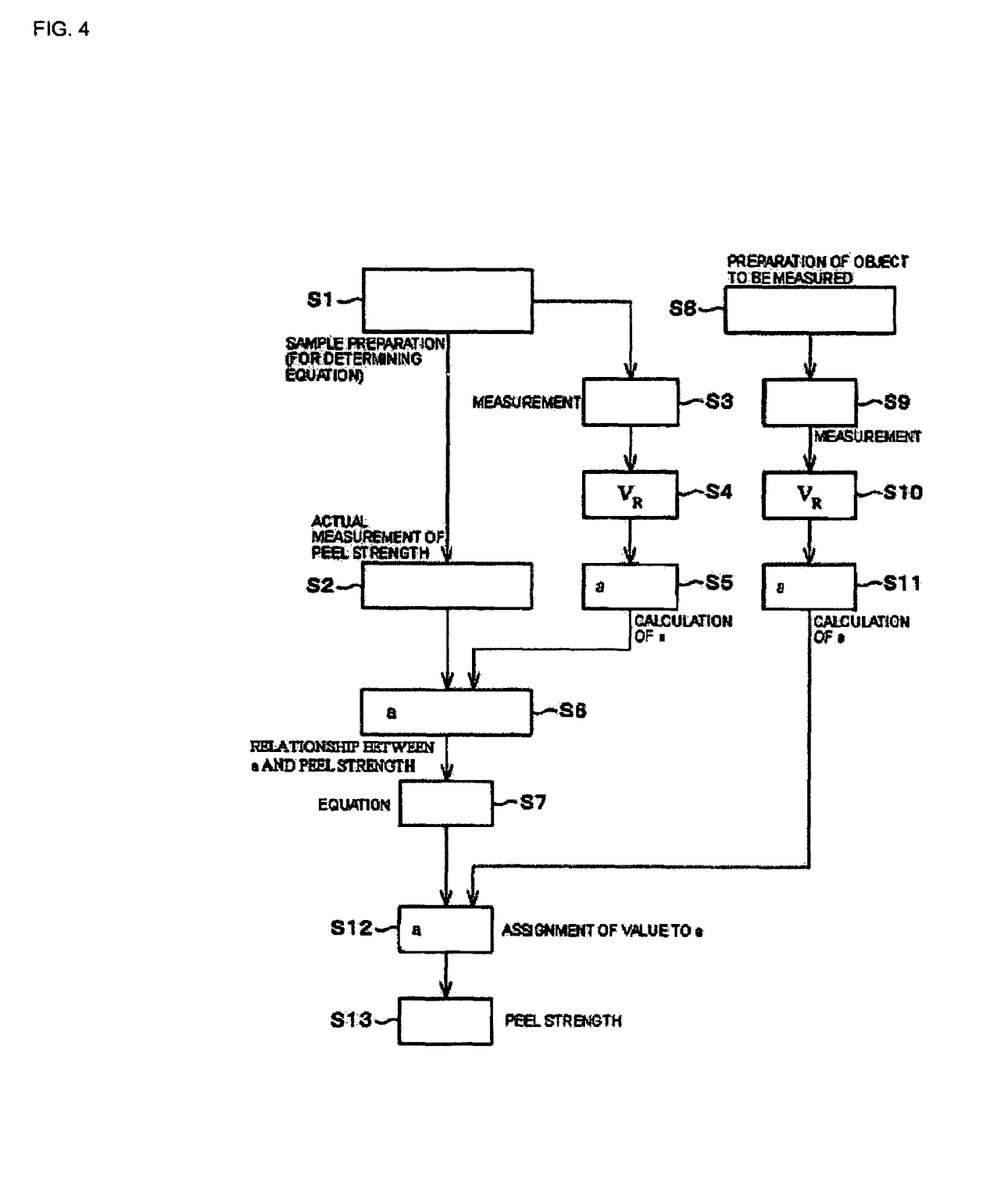
FIG. 4 is a flowchart showing the steps of determining an equation, and determining peel strength (film strength) using the equation, based on data obtained by measuring the object.

A method for obtaining an equation associated with the method for measuring film strength according to the present invention will now be described. As shown in FIG. 4, a first reference sample and a plurality of second reference samples are prepared (Step 1; hereinafter, the word "Step" will be abbreviated as "S"). The first reference sample has no separation and is made of a material similar to that of the object 8. The plurality of second reference samples have different levels of separation and are made of a material similar to that of the object 8. Each of the second reference samples is different in film-forming condition (acetone cleaning, ethanol cleaning, and aqueous cleaning).

Subsequently, a bond test determines the peel strength $\sigma_f$ of each second reference sample by actual measurement (S2). The results are shown in Table 1. The first reference sample, which includes the same base as that of the object 8, may have a film and may exhibit no $V_R$ region, or may have no film. Since it is difficult to obtain a sample with no separation when using the measuring and determining methods of the present invention in order to find a film-forming condition that tends not to cause a separation, it is preferable that a sample having no film is used as a first reference sample.

the peel strength $\sigma_f$ actually measured is determined (S6) to obtain an equation (S7), which is $\sigma=612\times a$ in the above-described case.

In addition, the object 8 with unknown film strength (indicated by "G" in Table 1) is prepared (S8) and measured (S9) similarly to S3, the intensity difference $V_R$ is measured (S10), and the bond strength a of the film is determined to be 1.3 (S11) in this case. This value of the bond strength a is assigned to the equation $\sigma=612\times a$ (S12) to yield the film peel strength 795 (S113). The results are shown in Table 1.

Figure 5:
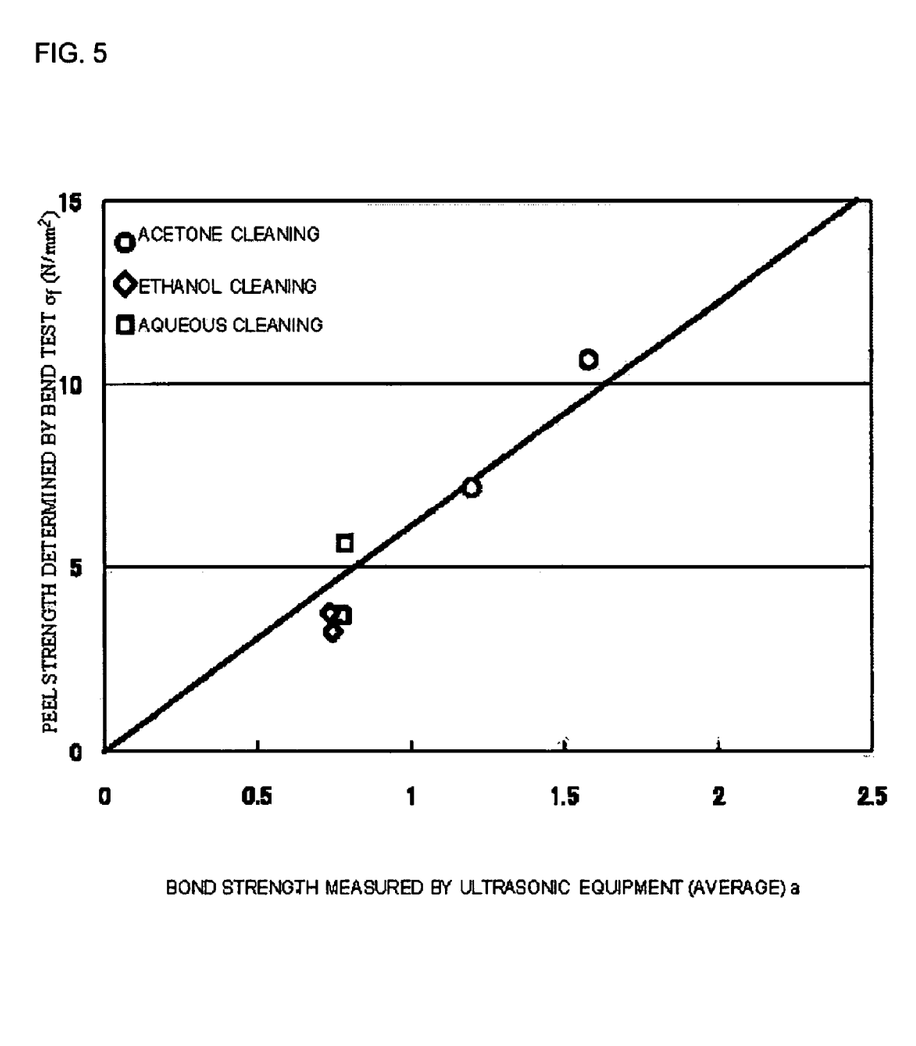
FIG. 5 is a graphic representation of the equation.

From the measurement described above, the relationship of $V_R$, $V_C$ (calculated in advance), $V_0'$ (substituted by $V_0$ described above), and the bond strength a of the film can be expressed as $a=V_R \cdot V_0/V_C^2$. This is based on the discovery by the present inventors that the bond strength a described above and the peel strength $\sigma_f$ obtained by the bend test have a proportional relationship as shown in FIG. 5, and that the film peel strength $\sigma_f$ can be quantitatively assessed by the bond strength a.

Figure 6:
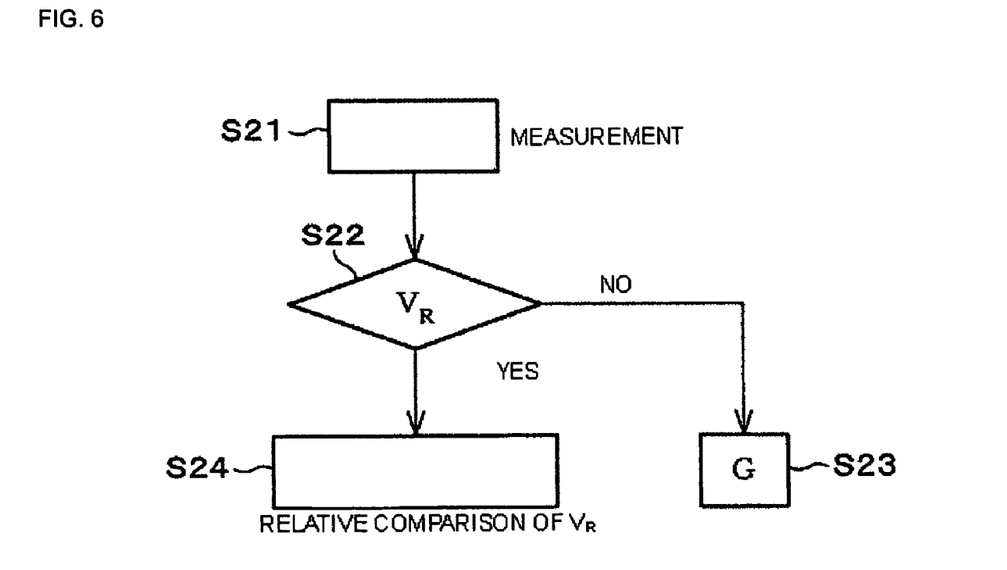
FIG. 6 is a flowchart showing a method for determining the quality of the object having a film.

A method for determining the quality of the object 8 having a film will now be described. First, the objects 8 having different film-forming condition (acetone cleaning, ethanol cleaning, and aqueous cleaning) are prepared. Subsequently, as shown in FIG. 6, each object 8 is measured at different incident angles using the method for measuring film strength according to the present invention (S21). A

TABLE 1

| Sample | A | B | C | D | E | F | G |
| --- | --- | --- | --- | --- | --- | --- | --- |
| $V_O$ | 0.1189 | 0.1192 | 0.1192 | 0.1189 | 0.1188 | 0.1190 | 0.1191 |
| $V_C$ | 0.0346 | 0.0346 | 0.0346 | 0.0346 | 0.0346 | 0.0346 | 0.0346 |
| $V_R$ | 0.0161 | 0.0121 | 0.0070 | 0.00705 | 0.00857 | 0.00855 | 0.01307 |
| a | 1.60 | 1.20 | 0.70 | 0.70 | 0.85 | 0.85 | 1.30 |
| Peel Strength | 1090 | 739 | 395 | 346 | 562 | 386 | 795 |

Referring to Table 1, the film-forming condition of Samples A and B is acetone cleaning, the film-forming condition of Samples C and D is ethanol cleaning, and the film-forming condition of Samples E and F is aqueous cleaning. The unit of $V_0$, $V_C$, and $V_R$ is mV, while the unit of peel strength is kg/mm$^2$.

Pressure waves are applied to the first reference sample at different incident angles to measure the received intensity (pressure-wave intensity) from the object 8. A received intensity (first intensity) when the incident angle of the pressure waves is a critical angle θcr and the leaky-wave intensity is high, and a received intensity $V_0$ (second intensity) when no leaky-wave intensity is detected, are measured to determine the intensity difference $V_C$ between the first intensity and the second intensity (S3).

Subsequently, pressure waves are applied to each second reference sample at different incident angles over the range including the critical angle θcr to measure the received intensity (pressure-wave intensity) from the object 8. Then, the intensity difference $V_R$ between a third intensity when the leaky-wave intensity remains unchanged and the received intensity $V_0$ is determined (S3 and S4). The results are shown in Table 1.

Then, a bond strength (bond strength index) a of a film is determined based on each intensity difference $V_R$ of each second reference sample (S5). The results are also shown in Table 1. The relationship between the bond strength a and reflected waveform corresponding to each incident angle is processed by an FFT method. Here, the relationship between the received intensity and the incident angle at a particular frequency is determined as a received intensity pattern.

The received intensity pattern is observed, for example, on the oscilloscope 5 or pattern recognition of the received intensity pattern is performed by the control unit 6, which determines whether the region $V_R$ appears (S22). When no $V_R$ region appears, the object 8 is determined to be a good component (G) (S23). When a region $V_R$ is present, a relative comparison between the value of the $V_R$ and pre-calculated values of the reference objects 8 are performed to determine the quality of the measured object 8 (S24).

The presence of the region $V_R$ is determined based on whether there is a region where the leaky-wave intensity remains unchanged, that is, the received intensity remains unchanged, even if the incident angle is changed by 0.1°. A value (mV) of $V_R$ in each object 8 is 0.0161 in acetone cleaning, 0.070 in ethanol cleaning, and 0.0857 in aqueous cleaning. Each film strength depends on the level of $V_R$.

In this method, the quality of the object 8 is determined by visual identification and relatively easy pattern recognition in which changes in received intensity, in response to changes in incident angles, is detected. Thus, a simple and quick determination of the quality of the object 8 can be achieved.

Second Embodiment

Figure 7:
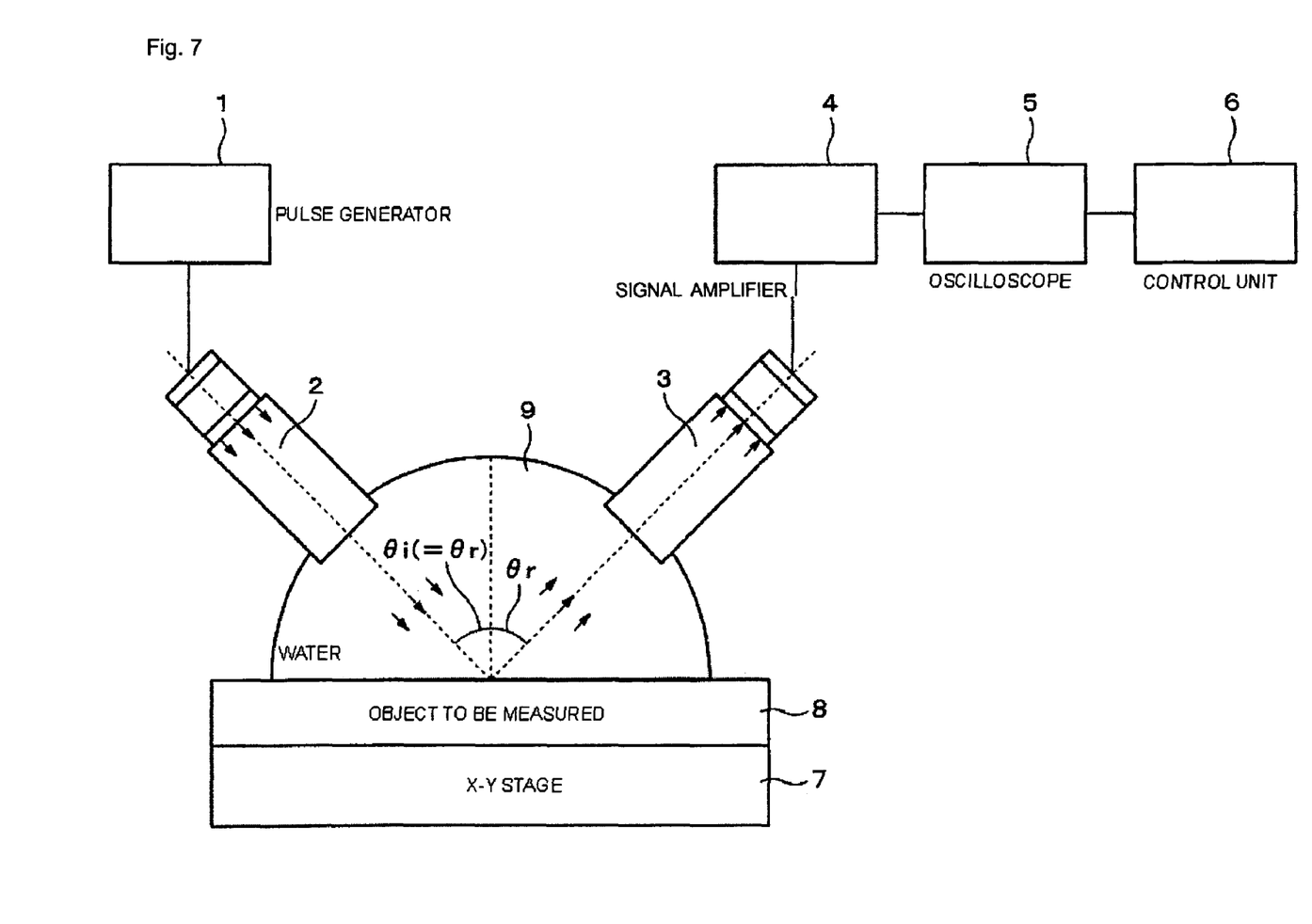
FIG. 7 is a block diagram of a measuring apparatus used in a method for measuring film strength according to a second embodiment of the present invention.

FIG. 7 shows a measuring apparatus used in a method for measuring film strength according to a second embodiment of the present invention. As shown, an X-Y stage 7 for horizontally and two-dimensionally moving the object 8 in the water 9 is added to the measuring apparatus of the first embodiment. The plurality of objects 8 can be separately placed on the X-Y stage 7.

In the method for measuring film strength according to the second embodiment, received intensity can be measured while the angle θi (=θr) of each of the transducers 2 and 3 is maintained. After the measurement, the X-Y stage 7 can be moved to change measuring points and repeat the measurement on the plurality of objects 8.

In the second embodiment, the received intensity when a film is firmly bonded to a base is measured in advance and stored for reference. The level of the peel strength of the film is determined based on the deviation of the received intensity at each measuring point from the reference.

The method for measuring film strength a nd the method for determining the quality of the object 8, according to the present invention, are suitable for use in producing an electronic component having a film, such as an external electrode. Examples of the electronic component include a chip laminated capacitor, laminated inductor, surface-acoustic-wave filter, acousto-optical tunable filter, and planar dielectric integrated-circuit. The acousto-optical tunable filter is a device for superimposing/extracting optical signals with a particular wavelength on/from a multiple-wavelength network. The planar dielectric integrated-circuit includes a high-frequency-dielectric substrate, a resonator, and other devices.

In the method for determining the quality of an object having a film according to the present invention, a criterion for determining the quality of the object can be changed by changing the output of the pressure waves to be applied to the object.

In this method, the output (pressure) of pressure waves can be changed by changing the voltage applied to the transducer 2. Then, Rayleigh waves excited by the pressure waves are changed, and thus the criterion for determining the quality of the object can be changed. For example, an increase in voltage applied to the transducer 2 excites and increases the Rayleigh waves. Since this increases a peel stress in a film, a stricter criterion can be set up for determining the quality of the object.

Although the present invention has been described in relation to particular embodiments thereof, many other variations and modifications and other uses will become apparent to those skilled in the art. Therefore, the present invention is not limited by the specific disclosure herein.

What is claimed is:

1. A method for measuring a film strength of a film on an object, comprising the steps of:
    setting an incident angle of pressure waves with respect to an object to be measured, the object comprising a base coated with a film, for applying the pressure waves to the object;
    varying the incident angle over a range including a critical angle, thereby allowing the object to generate surface waves, in response to the pressure waves, at and near the critical angle; and thereby allowing the object to generate leaky waves, the leaky waves being pressure waves caused by the surface waves;
    measuring an intensity of received pressure waves from the object, the received pressure waves including reflected waves and the leaky waves; and
    determining the film strength of the object based on changes in the intensity of the leaky waves from the object in response to changes in the incident angle.

2. The method for measuring a film strength according to claim 1, wherein the step of determining the film strength of the object further comprises the substep of determining whether a film separation occurs in the object, based on the presence or absence of a region where the intensity of the leaky waves remains unchanged regardless of the changes in the incident angle.

3. The method for measuring a film strength according to claim 1, further comprising the step of immersing an object in an inelastic fluid in advance.

4. The method for measuring a film strength according to one of claims 1 to 3, further comprising the steps of:
    measuring the film strength of each of a plurality of objects; and
    comparing the measured film strengths to evaluate the relative film strength of each of the objects.

5. The method of measuring a film strength according to one of claims 1 to 3, further comprising the step of moving the object transversely with respect to said applied pressure waves to set a new measuring point for measuring said film strength at said new measuring point.

6. A method for determining a quality of an object having a film, comprising the steps of:
    setting an incident angle of pressure waves with respect to an object to be measured, the object comprising a base coated with a film, for applying the pressure waves to the object;
    varying the incident angle over a range including a critical angle, thereby allowing the object to generate surface waves, in response to the pressure waves, at and near the critical angle, and thereby allowing the object to generate leaky waves, the leaky waves being pressure waves caused by the surface waves;
    measuring an intensity of received pressure waves from the object, the received pressure waves including reflected waves and the leaky waves; and
    determining a film strength of the object based on changes in the intensity of the leaky waves from the object in response to changes in the incident angle, wherein
    the step of determining the film strength of the object further comprises the substep of determining whether a film separation occurs in the object, based on the presence or absence of a region where the intensity of the leaky waves remains unchanged regardless of the changes in the incident angle; and wherein
    the quality of the object is determined based on the presence or absence of a film separation.

7. The method for determining a quality of an object having a film, according to claim 6, wherein a criterion for determining the quality of the object can be changed by changing the intensity of the pressure waves to be applied to the object.

8. The method for determining a quality of an object having a film, according to claim 6, further comprising the step of moving the object transversely with respect to said applied pressure waves to set a new measuring point for measuring said film strength at said new measuring point.

9. A method for measuring a film strength and detecting a separation in a film on an object, comprising the steps of:
    setting an incident angle of pressure waves with respect to an object to be measured, the object having a film on a surface, for applying the pressure waves to the object, and measuring pressure waves including reflected waves and leaky waves from the object to determine the strength of the film, the method further comprising the steps of:

preparing, in advance, a first reference sample having no separation and made of a material similar to that of the object, applying the pressure waves to the first reference sample at varying incident angles, measuring an intensity of the pressure waves received from the object, the intensity including a first intensity $V_O$ when the incident angle of the pressure waves is a critical angle and the leaky-wave intensity is high, and a second intensity when no leaky-wave intensity is detected, and thereby determining an intensity difference $V_C$ between the first intensity and the second intensity;

preparing, in advance, a plurality of second reference samples each having separations and being made of a material similar to that of the object, applying the pressure waves to the second reference samples at varying incident angles over the range including the critical angle, measuring the intensity of the pressure waves received from the object; and thereby determining an intensity difference VR between a third intensity when the leaky-wave intensity remains unchanged regardless of changes in the incident angle, and the second intensity;

measuring a peel strength of each second reference sample by an actual measurement to determine a relationship between the measured peel strength and a bond strength index a; and determining the peel strength of the film of the object based on the relationship between the peel strength and the bond strength index a, and the intensity difference $V_R$ of the object.

10. The method for measuring a film strength according to claim 9, wherein the step of determining the peel strength of the film of the object utilizes the equation $$a = (V_R \cdot V_0)/V_C^2.$$

11. The method for measuring a film strength according to claim 9, further comprising the step of moving the object transversely with respect to said applied pressure waves to set a new measuring point for measuring said film strength at said new measuring point.

* * * * *